(12) United States Patent
Chen et al.

(10) Patent No.: US 6,977,103 B2
(45) Date of Patent: *Dec. 20, 2005

(54) DIMENSIONALLY STABLE BALLOONS

(75) Inventors: John Jianhua Chen, Plymouth, MN (US); Lixiao Wang, LongLake, MN (US); Yiqun Wang, Maple Grove, MN (US); Albert C. C. Chin, Newton, MA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 329 days.

This patent is subject to a terminal disclaimer.

(21) Appl. No.: 09/885,568

(22) Filed: Jun. 20, 2001

(65) Prior Publication Data

US 2001/0043998 A1 Nov. 22, 2001

Related U.S. Application Data

(63) Continuation-in-part of application No. 09/696,378, filed on Oct. 25, 2000, now Pat. No. 6,905,743, which is a continuation-in-part of application No. 09/426,384, filed on Oct. 25, 1999, now abandoned.

(51) Int. Cl.[7] .................. A61M 29/00; A61M 25/10
(52) U.S. Cl. ............ 428/35.7; 604/96.01; 604/103.09; 604/103.11; 604/524; 264/108; 264/171.27; 264/171.28
(58) Field of Search .................. 428/35.7; 604/96.01, 604/524, 103.09, 103.11; 264/108, 171.27, 264/171.28, 175.15; 525/314

(56) References Cited

U.S. PATENT DOCUMENTS

| | | | |
|---|---|---|---|
| 3,825,036 A | 7/1974 | Stent | 138/174 |
| 3,991,014 A | 11/1976 | Kleinschuster | 260/47 |
| 4,067,852 A | 1/1978 | Calundann | 260/47 |
| 4,083,829 A | 4/1978 | Calundann et al. | 260/47 |
| 4,130,545 A | 12/1978 | Calundann | 260/40 |
| 4,154,244 A | 5/1979 | Becker | 128/349 |
| 4,161,470 A | 7/1979 | Calundann | 260/40 |
| 4,222,384 A * | 9/1980 | Birtwell | 604/103 |
| 4,254,774 A * | 3/1981 | Boretos | 604/271 |
| 4,318,842 A | 3/1982 | East et al. | 524/605 |
| 4,331,786 A | 5/1982 | Foy et al. | 525/408 |
| 4,386,174 A | 5/1983 | Cogswell et al. | 524/27 |

(Continued)

FOREIGN PATENT DOCUMENTS

DE 0 448 886 A1 10/1991

(Continued)

OTHER PUBLICATIONS

P. Peyser, "Glass Transition Temperatures of Polymers" in Polymer Handbook 3rd ed. J. Brandrup and E.H. Immergut eds., VI-258-259.

(Continued)

Primary Examiner—Harold Pyon
Assistant Examiner—Sow-Fun Hon
(74) Attorney, Agent, or Firm—Vibas, Arrett & Steinkraus (57) ABSTRACT

An inflatable medical balloon comprises a polymer matrix material and a plurality of fibers distributed in the matrix material. The plurality of fibers operatively adhere to the matrix material and provide reinforcement thereof. The fibers may be parallel or angularly oriented relative to the longitudinal balloon axis, and may be helically disposed thereabout. The fibers may be composed of material which has a greater tensile strength than the matrix material. The fibers may be microfibers formed by phase separation of a melt blend material during extrusion or polymer cores coextruded with the matrix material and surrounded thereby. The balloon may be formed of alternating layers of fiber-free polymer and layers of fiber-containing polymer.

17 Claims, 4 Drawing Sheets

U.S. PATENT DOCUMENTS

| | | | |
|---|---|---|---|
| 4,412,059 A | 10/1983 | Krigbaum et al. | 528/192 |
| 4,417,021 A | 11/1983 | Naakamura | 524/538 |
| 4,433,083 A | 2/1984 | Cogswell et al. | 524/27 |
| 4,438,236 A | 3/1984 | Cogswell et al. | 525/165 |
| 4,444,817 A | 4/1984 | Subramanian | 428/36 |
| 4,448,195 A | 5/1984 | LeVeen | 12/344 |
| 4,468,364 A | 8/1984 | Ide | 264/176 |
| 4,829,683 A | 5/1989 | Chikamori et al. | 36/51 |
| RE32,983 E | 7/1989 | Levy | 428/36.92 |
| 4,963,313 A | 10/1990 | Noddin et al. | 264/573 |
| 5,059,751 A | 10/1991 | Woodman et al. | 200/61.45 |
| 5,156,785 A * | 10/1992 | Zdrahala | 264/108 |
| 5,195,969 A | 3/1993 | Wang et al. | 604/96 |
| 5,248,305 A | 9/1993 | Zdrahala | 604/280 |
| 5,254,089 A | 10/1993 | Wang | 604/96 |
| 5,264,260 A | 11/1993 | Saab | 428/35.5 |
| 5,270,086 A | 12/1993 | Hamlin | 428/35.2 |
| 5,290,306 A | 3/1994 | Trotta et al. | 606/194 |
| 5,304,340 A | 4/1994 | Downey | 264/521 |
| 5,306,246 A | 4/1994 | Sahatjian et al. | 604/280 |
| 5,328,468 A | 7/1994 | Kaneko et al. | 604/96 |
| 5,330,428 A | 7/1994 | Wang | 604/96 |
| 5,348,538 A | 9/1994 | Wang et al. | 604/96 |
| 5,358,486 A | 10/1994 | Saab | 604/96 |
| 5,389,314 A | 2/1995 | Wang | 264/25 |
| 5,427,842 A * | 6/1995 | Bland et al. | 428/213 |
| 5,441,489 A | 8/1995 | Utsumi et al. | 604/280 |
| 5,447,497 A | 9/1995 | Sogard et al. | 604/101 |
| 5,456,674 A | 10/1995 | Bos et al. | 604/280 |
| 5,458,572 A | 10/1995 | Campbell et al. | 604/96 |
| 5,512,051 A | 4/1996 | Wang et al. | 604/96 |
| 5,554,120 A | 9/1996 | Chen et al. | 604/96 |
| 5,556,383 A | 9/1996 | Wang et al. | 604/96 |
| 5,565,530 A | 10/1996 | Hattori et al. | 525/419 |
| 5,587,125 A | 12/1996 | Roychowdhury | 264/515 |
| 5,647,848 A | 7/1997 | Jorgensen | 604/96 |
| 5,702,418 A | 12/1997 | Ravenscroft | 606/198 |
| 5,704,913 A | 1/1998 | Abele et al. | 604/101 |
| 5,733,980 A | 3/1998 | Cozewith et al. | 525/314 |
| 5,755,690 A | 5/1998 | Saab | 604/96 |
| 5,797,877 A | 8/1998 | Hamilton et al. | 604/96 |
| 5,807,327 A | 9/1998 | Green et al. | 604/96 |
| 5,830,182 A | 11/1998 | Wang et al. | 604/96 |
| 5,833,657 A | 11/1998 | Reinhardt et al. | 604/101.02 |
| 5,863,488 A | 1/1999 | Moriya | 264/512 |
| 5,976,120 A | 11/1999 | Chow et al. | 604/525 |
| 6,024,722 A * | 2/2000 | Rau et al. | 604/96.01 |
| 6,036,697 A * | 3/2000 | DiCaprio | 606/108 |
| 6,059,751 A | 5/2000 | Ostapchenko et al. | 604/96 |
| 6,086,556 A | 7/2000 | Hamilton et al. | 604/96 |
| 6,124,007 A | 9/2000 | Wang et al. | 428/35.2 |
| 6,136,258 A | 10/2000 | Wang et al. | 264/514 |
| 6,156,842 A | 12/2000 | Hoenig et al. | 525/171 |
| 6,242,063 B1 | 6/2001 | Ferrera et al. | 428/35.2 |
| 6,284,333 B1 | 9/2001 | Wang et al. | 428/35.5 |
| 6,325,780 B1 | 12/2001 | Schaible et al. | 604/103.06 |
| 6,443,925 B1 | 9/2002 | Schaible et al. | 604/96.01 |
| 2001/0019751 A1 | 9/2001 | Ferrera et al. | |
| 2002/0045017 A1 | 4/2002 | Wang et al. | |

FOREIGN PATENT DOCUMENTS

| | | |
|---|---|---|
| DE | 0 934 755 A2 | 8/1999 |
| DE | 00/50105 | 8/2000 |
| EP | 0 369 734 | 5/1990 |
| EP | 0 420 488 | 4/1991 |
| EP | 0 934 755 A2 | 8/1999 |
| EP | 1 008 363 | 6/2000 |
| WO | 92/08512 | 5/1992 |
| WO | 92/19316 | 11/1992 |
| WO | 92/19440 | 11/1992 |
| WO | 93/24574 | 9/1993 |
| WO | WO 95/18647 * | 7/1995 |
| WO | 95/23619 | 9/1995 |
| WO | 96/00752 | 1/1996 |
| WO | 96/04951 | 2/1996 |
| WO | 97/24403 | 7/1997 |
| WO | 97/32624 | 9/1997 |
| WO | 99/12586 | 3/1999 |
| WO | 01/34062 | 5/2001 |

OTHER PUBLICATIONS

P.J. Collings, "Liquid Crystals, Nature's Delicate Phase of Matter", pp. 20-23, 162-180 (1990).

I.C. Khoo, "Liquid Crystals Physical Properties and Nonlinear Optical Phenomena", p. 5-11, 1995.

Hal-Garcia Cardiology Associates, May 1, 2000, Percutaneous Transluminal Coronary Aigioplasty http:www.hgcardio.com/ptc.

Polymers- A Property Database Copyright CRC Press, LLC, 2000.

Alger, Polymer Science Dictionary, 2$^{nd}$ Edition, 1997.

Yong Yang, Hydroxypropylcellulose, Polymer Data Handbook, Oxford University Press, Copyright 1999.

J.P. DeSouza et al., "Processing Studies of In Situ Composites Based on Blends on Liquis Crystalline Polymers With Engineering Thermoplastics", *Polymer Preprints*, 392-393 Apr. 1992.

Q. Lin and A.F. Yee, Measurement of Molecular Orientation of Liquid Crystalline Polymer *in situ* Composites by X-Ray Scattering Technique, *Polymer Preprints*, pp. 298-299, Apr. 1992.

J.M. Schultz, "Structure Evolution In PET Fibers". *Polymer Preprints*, 304-306 Apr. 1992.

J. Liu et al., "Crystal Structure and Transitions in Rigid Rod Thermotropic Liquid Crystal Polymers", *Polymer Preprints*, 337-338 Apr. 1992.

J.G. Harris and Y. Wang, "Molecular Dynamics Studies of Branched and Linear Hydrocarbons at Liquid-Vapor and Liquid-Solid Interfaces", *Polymer Preprints*, 539-540, Apr. 1992.

W.J. Farrissey and T.M. Shah, Polyamide Thermoplastic Elastomers, in Handbook of Thermoplastic Elastomers, B. M. Walker and C.R. Rader, eds., pp. 258-281.

B.N. Epstein et al., "Polymer Blends-An Overview"., *Polymer Preprints*, 42-43, Jun. 1991.

M.M. Coleman et al., "Miscibility Maps for Copolymer—Copolymer Blends: A Comparison of Theoretical Predicitions to Experimental Data", *Polymer Preprints*, 44-45, Jun. 1991.

W.M. Cheng et al., "Main Chain-Side Chain Liquid Crystal Polymer Blends for Improved Physical Properties", *Polymer Preprints*, 50-51, Jun. 1991.

R.R. Matheson, Jr., "Polymers, Processes and Additives as Systems", *Polymer Preprints*, 52-53, Jun. 1991.

S. Allen et al., "The Effect of Additives on Tensile Properties of PPD-T Fibers", *Polymer Preprints*, 54-55, Jun. 1991.

J.R. Runt et al., "Phase Behavior and Crystallization in Blends of Poly(butyleneterephthalate) and Polyarylate", *Polymer Prepritns*, 56-57, Jun. 1991.

T.W. Cheng et al., "Property and Morphology Relationships for Ternary Blends of Polycarbonate, Brittle Polymers, and an Impact Modifier", *Polymer Preprints*, 58-59, Jun. 1991.

M.M. Nir and R.E. Cohen, "Compatibilization of Blends of Crystallizable Polybutadiene Isomers by Precipitation and by Addition of Amorphous Diblock Copolymer", *Polymer Preprints*, 60-61, Jun. 1991.

U.M. Vakil and G.C. Martin, "Analysis of Structure-Property Relations in Crosslinked Epoxies", *Polymer Preprints*, 62-63, Jun. 1991.

Superex Polymer, Inc. press release, "Dual Compatibilized Recyclable PET-LCP Alloys with Enhanced Barrier and Structural Performance".

Hoechst Celanese Vectra © Liquid Crystal Polymer Product Information.

Superex Polymer, Inc Advertisement, "Building product value through new processing and application technologies".

Xydar© product data, Sep. 1994.

Amoco Engineering Plastics for Performance and Value product brochure.

B. Miller, "Rotating Dies Pave Way for Extruding LCP", Plastics World.

A.M. Adur and L.J. Bonis, "PET-LCP Compatibilized Alloys: A New Unique Development".

G.C. Rutledge, "Modelling Chain Rigidity and Orientation in Liquid Crystalline Polymers", *Polymer Preprints*, 537-538, Apr. 1992.

R.K. Menon, "Kinetic Theory for Liquid Crystalline Polymer Solutions", *Polymer Preprints*, 574-575, Apr. 1992.

O.V. Noah and N.A. Plate, "Simulation of Macromolecules Conformations in Processes of Intra and Intermolecular Crosslinking", *Polymer Preprints*, 578-579, Apr. 1992.

H. Boublil et al., "Morphology of Polyamide and Polyether Block Amide Blends", *Polymer Enginnering and Science*, vol. 29, No. 10, 679-684, May 1989.

E. Okoroafor and J. Rault, "Cryodilation of Thermoplastic PEBA Elastomers", *J. Polymer Sci: Part B: Polmer Physics*, Vopl. 29, 1427-1436, 1991.

E. Barmatov et al., "Oriented Networks of Comb-Shaped Liqiud Crystalline Polymers", *Polymer Preprints*, 706-707, Aug. 1993.

M. Brehmer et al., "LC-Elastomers by Chemical and Physical Crosslinking", *Polymer Preprints*, 708-709, Aug. 1993.

A.Y. Bilibin and A.R. Stepanova, "Synthesis of Liquid Crystalline Multiblock Copolymers With Definite Structure of Rigid Block", *Polymer Preprints*, 714-715, Aug. 1993.

Y. Yang et al., Orientation and Strain-Induced Liquid-Crystalline Phase Transition of Networks of Semi-Rigid Chains, *Polymer Preprints*, 729-730, Aug. 1993.

R. Stadler and T. Oehmichen, "Telechelic Oligoaramides—A Means for Rigid-Rod Molecular Inforcement of Thermoplastic Materials", *Polymer Preprints*, 731-733, Aug. 1993.

D.H. Weinkauf and D.R. Paul, "The Influence of Molecular Architecture on Gas Transport Properties of Liquid Crystalline Polymers", *Polymer Preprints*, 372-373, Aug. 1991.

P.A. Rodgers and I.C. Sanchez, "Gas Solubility in Polymers and Blends", *Polymer Preprints*, 392-393, Aug. 1991.

W. Brostow, "Properties of Polymer Liquid Crystals: Choosing Molecular Structures and Blending", *Polymer*, vol. 31, 979-995, Jun. 1990.

R.J. Lewis, Sr., "Hawley's Condensed Chemical Dictionary, 12$^{th}$ ed." Pp. 704, 932-934, 936-939 (1993).

Kirk-Othmer Concise Encyclopedia of Chemical Technology, pp. 148-149, 391-395, 814-819, 924-939 (1985).

U.S. Appl. No. 09/426,384, filed Oct. 25, 1999, Chen et al.

U.S. Appl. No. 09/696,378, filed Oct. 25, 1999, Wang et al.

\* cited by examiner

DIMENSIONALLY STABLE BALLOONS

CROSS-REFERENCE TO RELATED APPLICATIONS

This application is a continuation-in-part of U.S. application Ser. No. 09/698,378, filed Oct. 25, 2000, now U.S. Pat. No. 6,905,743, which is a continuation-in-part of U.S. application Ser. No. 09/426,384, filed Oct. 25, 1999, now abandoned.

BACKGROUND OF THE INVENTION

Medical catheters having a balloon mounted thereon are useful in a variety of medical procedures. A balloon may be used to widen a vessel into which the catheter is inserted by dilating the blocked vessel, such as in an angioplasty procedure. Some examples of stent delivery balloons are disclosed in U.S. Pat. No. 5,702,418, and U.S. Pat. No. 5,797,877, the entire contents of both patents is hereby incorporated by reference. In these and other medical device delivery applications, radial expansion of a balloon may be used to expand or inflate a stent at a desired positioned within the body. Using a balloon equipped catheter to deliver a stent requires precise positioning of the balloon and stent as well as a balloon with accurate and predictable expansion properties. A known drawback of many previous delivery catheters and balloons is that when a balloon is radially inflated to a desired extent, the balloon will also expand longitudinally. As a result of longitudinal expansion of a balloon during the delivery of a medical device, the balloon itself, the medical device mounted thereupon or both apparatuses may be shifted from their pre-inflation position resulting in improper delivery of the medical device.

In balloons where longitudinal expansion occurs, the balloon may expand longitudinally past one or both of the stent ends. Typical stent delivery balloons will expand longitudinally at least 5% beyond the original pre-inflation state. In addition to potentially mis-delivering the medical device as described above, the resulting extended balloon may cause the edges of the stent to push against the vessel wall to a greater extent than they would from radial expansion alone.

It has recently been discovered that Liquid Crystal Polymers (LCP) may be effectively blended with other materials and extruded to form high strength medical balloons. In copending U.S. applications Ser. No. 08/926,905 (corresponding to PCT/US98/18345 filed Sep. 4, 1998), and 09/257,677 filed Feb. 25, 1999 there are described medical balloons made from LCP blends. The entire contents of both of these applications is hereby incorporated by reference.

U.S. Pat. No. 5,389,314 to Wang discloses an inflatable medical device which has a plurality of longitudinally oriented conduits which extend through out the length of the device. The device may be formed by co-extruding two dissimilar plastic materials. The first material form defining a discrete phase which forms fibers and the other material or continuous phase which forms the remaining balloon material. After extrusion the discrete phase is withdrawn from the continuous phase, leaving the continuous phase with a plurality of conduits therethrough.

BRIEF SUMMARY OF THE INVENTION

The present invention is directed generally to medical balloons which expand only to a predetermined extent, and which have minimal longitudinal and/or minimal radial growth during expansion. Specifically, the invention is directed to a stent delivery balloon composed of a micro-composite material which includes a longitudinal fibril structure that is either parallel to the longitudinal axis of the balloon structure, or that is angularly disposed relative to the longitudinal axis at the molecular level of the balloon. The orientation of the fibril structure can limit longitudinal expansion of the balloon and allow the balloon to expand radially as desired, but minimally, or not at all in the longitudinal direction if the fibrils are parallel to the balloon axis, or when the fibrils are oriented diagonally about the axis, can limit both, longitudinal and radial expansion of the balloon when inflated.

The micro-composite material is made up of a combination of a fibril component, a semi-compliant balloon material which acts as a matrix, and optionally a compatibilizer material which may act to create a less distinctive phase boundary between the fibril and matrix components, but which does not solubilize the LCP polymer in the matrix at human body temperature.

The present invention provides for a balloon which utilizes LCP materials or other oriented materials such as PET, in combination with a thermoplastic elastomer matrix and an optional compatibilizer to form a micro-composite material. The present micro-composite material is suitable for construction balloons which exhibit minimal or no longitudinal growth during balloon expansion but which expands as desired in the radial direction, or the present micro-composite material is suitable for construction of balloons that exhibit minimal expansion both in the longitudinal and radial directions.

BRIEF DESCRIPTION OF THE SEVERAL VIEWS OF THE DRAWINGS

A detailed description of the invention is hereinafter described with specific reference being made to the drawings in which.

DETAILED DESCRIPTION OF THE INVENTION

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

As noted above, the present invention relates to medical catheters which have one or more balloon portions constructed from a specially configured micro-composite material. The particular micro-composite material and configuration provides physical properties which allow a balloon to expand radially to a predetermined extent, but which allow only minimal, or more preferably, no longitudinal growth during expansion. The micro-composite material includes a longitudinal fibril component which exhibits micro-fibers in combination with a matrix of any semi-compliant balloon material. Depending on the specific fibril component, as well as the method of extrusion utilized to extrude the balloon material, the micro-fibers may be randomly scattered through out the balloon material or may be precisely spaced about the balloon and extending through the entire balloon length. The fibril structure is oriented or directed in the longitudinal direction of the balloon providing the balloon with desirable radial expansion characteristics and minimal longitudinal growth when the balloon is inflated.

Figure 1:
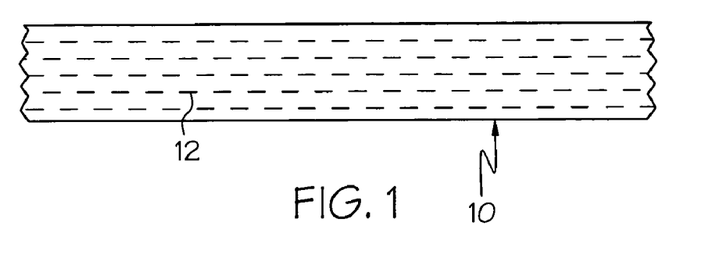
FIG. 1 is a schematic representation of side view of a tubular parison used to produce a balloon of the invention from a the micro-fiber composite material.

As shown in FIG. 1, the balloons of the invention may be made from tubular parisons 10 of the micro-composite material, having a fibril component which exhibits micro-fibers 12 uniformly oriented in a predetermined direction. In a preferred embodiment shown in FIG. 2, the micro-composite is formed into a balloon 20 from a parison 10 by a conventional balloon blowing process. Balloon 20 has a diameter D and a length L. Micro-fibers 12 are oriented along and about the longitudinal axis 22 of the balloon. The fibril component may be any rigid-rod or semi-rigid-rod thermoplastic material which comprises 0.1 to about 25 percent, and more preferably from about 0.5 to about 20 percent by weight of the micro-composite material. Examples of suitable materials which could be utilized as the fibril component include: liquid crystal polymers such as VECTRA® LKX 1107, 1111, polyetheretherketone (PEEK) material, and PPS. Other materials may also be utilized as the fibril component of the present invention. Such substances include aromatic nylon, rigid polyurethane, polyester, copolyester, polyester blends, polyester/polyurethane blends, PEEK, PPS, fluoropolymer and so on.

The diameter of the fiber 12 may be 0.01 micron or larger, and may have a thickness substantially equal to the balloon. The length of the fiber 12 may range from as small as 0.02 microns to being substantially the same length of the balloon.

To form the micro-composite material, the fibril component is preferably combined with a semi-compliant thermoplastic polymer material in a melt blend which at least partially phase separates upon cooling. Under appropriate conditions the phase separated material will form fibrils or micro-fiber 12 embedded in a matrix of the semi-compliant thermoplastic polymer, oriented substantially parallel to the longitudinal axis of the extruded tubing. The micro-composite material suitably employs an amount of semi-compliant polymer matrix component from about 50 to 99.9 percent by weight, preferably from about 85 to 99.5 percent.

Some examples of suitable materials which may be utilized as the matrix component are polyamide-polyether block copolymers, namely the polyamide/polyether/polyesters PEBAX® 6333, 7033 and 7233; also polyester-polyether block copolymer such as ARNITEL® EM740.

As previously described, the present invention achieves the desired balloon expansion characteristics as a result of forming a balloon composed of a micro-composite material. The micro-composite material balloon is formed by coextrusion of a melt blend of LCP or other orientable material, the matrix component, and optionally a compatibilizer. A dual extrusion process utilizing two extruders may also be used to form the desired tube. The shear rate at die exit can be in the range of about 200 $\sec^{-1}$, to about 1500 $\sec^{-1}$. Where LCP is used as the fibril component, the shear rate may be about 400 $\sec^{-1}$ to about 100 $\sec^{-1}$. If the LCP is not subjected to a sufficient shearing force, the LCP will form droplet shaped deposits which provide minimal or no longitudinal stabilization.

If, during extrusion, relative rotation of the mandrel and die is avoided, the fibrils will adopt an orientation substantially parallel to the longitudinal axis. If the die and mandrel are relatively rotated, e/g. by rotation of one or the other or both, the orientation of the fibrils will be helically about the axis.

A balloon which has an LCP fibril component tends to have individual fibers spread randomly throughout the balloon material. The individual LCP fibers will typically be between 0.01 micron to 10 microns in diameter.

If the various components utilized to form the micro-composite material are incompatible to a substantial degree, phase separation may be so efficient that slippage between phases might occur during balloon expansion thereby reducing the longitudinal restriction effect of the fibrils. To prevent such occurrences a compatibilizer may also be desirable for the purpose of enhancing the homogeneity of the melt blend prior to extrusion and cooling. A compatibilizer material may be added to the pre-extruded melt blend material to create a less distinctive phase boundary between the fibril and matrix components. The compatibilizer may be for instance a block copolymer comprising a block which is structurally similar or otherwise is soluble in the matrix polymer and a block which is structurally similar or otherwise soluble with the fibril component.

The compatibilizers include copolyester elastomers; ethylene unsaturated ester copolymers, such as ethylene-maleic anhydride copolymers; copolymers of ethylene and a carboxylic acid or acid derivative, such as ethylene-methyl acrylate copolymers; polyolefins or ethylene-unsaturated ester copolymers grafted with functional monomers, such as ethylene-methyl acrylate copolymers; copolymers of ethylene and a carboxylic acid or acid derivative, such as ethylene-methyl acrylate-maleic anhydride terpolymers; terpolymers of ethylene, unsaturated ester and a carbloxylic acid or acid derivative, such as ethylene-methyl acrylate-methacrylic acid terpolymers; maleic acid grafted styrene-ethylene-butadiene-styrene block copolymers; and acrylic elastomers, such as acrylic rubbers. Similar polymers containing epoxy functional groups, for instance derived from glycidyl methylacylate, in particular, alkyl (meth)acrylate-ethylene-glycidyl (meth)acrylate polymers can also be usefully employed. Monomeric copolymers can be employed as compatabilizers. Specific suitable compatabilizers include the copolyester elastomer, Hytrel™ HTR-6108 (DuPont); the ethylene-maleic anhydride copolymer, Polybond™ 3009 (BP Chemicals); the ethylene-methyl acrylate copolymer, SP 2205 (Chevron); the ethylene-methyl acrylate copolymer grafted with maleic anhydride, DS 1328/60 (Chevron); the ethylene-methyl acrylate-maleic anhydride terpolymer, Lotader™ 2400; the ethylene-methyl acrylate-maleic acid terpolymers, Escor™ ATX-320, Escor™ ATX-325 or Escor™ XV-11.04; the acrylic rubber, Vamac™ G1 and the ethylene-ethyl acrylate-glycidyl methacrylate terpolymer, Lotader™ AX 8660.

A compatibilizer may be employed in an amount from 0 to about 30 weight percent of the total composition.

Figure 2:
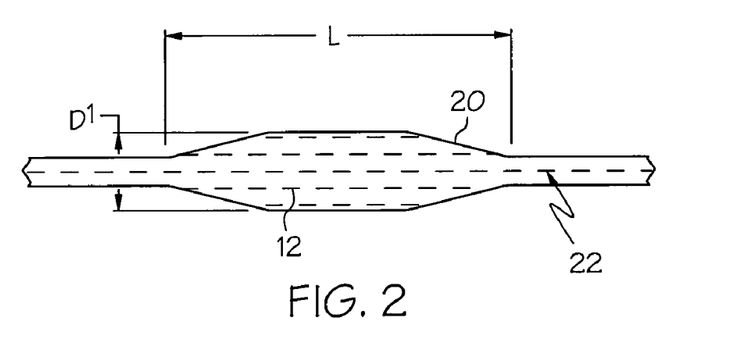
FIG. 2 is a schematic side view of a medical device delivery balloon constructed from micro-composite material shown at nominal diameter wherein the fibril component is oriented parallel to the longitudinal balloon axis.
Figure 3:
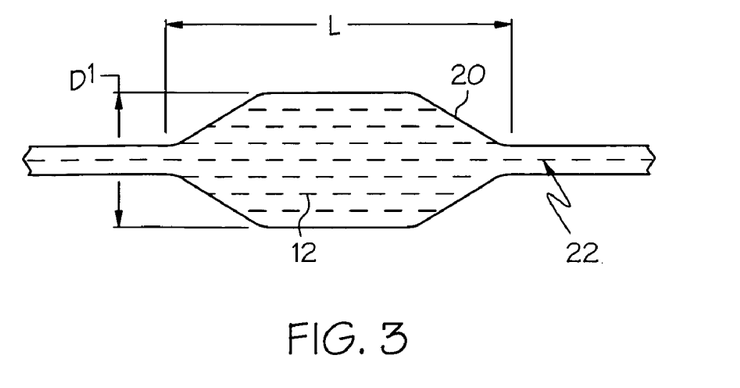
FIG. 3 is a view of the medical device delivery balloon shown in FIG. 2 in an inflated state at a pressure higher which causes radial growth of the balloon.

The balloon 20, shown in FIG. 2 at nominal diameter, is shown in FIG. 3 inflated at a higher pressure which provides radial expansion to a new, larger diameter D'. In the most preferred embodiment, the micro-composite material 10 allows balloon 20 to obtain semi-compliant expansion in the radial direction with reduced balloon expansion in the longitudinal direction during inflation (balloon length L is substantially unchanged in FIG. 3). In some embodiments, longitudinal expansion is less than 10 percent, typically less than 8 percent and in some embodiments less than 6 percent from nominal. Depending on the precise mixture and type of matrix and fibril components used, other embodiments of the present invention may provide for balloons with varying degrees and types of radial expansion while also reducing longitudinal expansion by varying degrees.

If substances less prone to phase separation from the matrix material are desired to be used, an appropriately shaped die may be used in the extrusion process to provide individually extruded fibers evenly around the tube circumference, for instance in the manner of U.S. Pat. No. 5,389,314 except that the fiber material is selected to adhere to the matrix material and a high line speed is used to provide a microscopic fiber diameter. For such an embodiment, the individual non-LCP fibers may be between about 5–20 microns and in particular embodiments may be between about 10–12 microns in diameter and may also extend through the entire length of the balloon in chain or cores.

Figure 4:
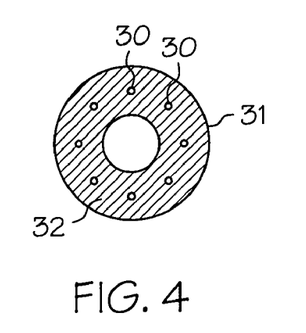
FIG. 4 is a cross-sectional view of a tubular parison for producing balloon of an alternative embodiment of the invention.
Figure 5:
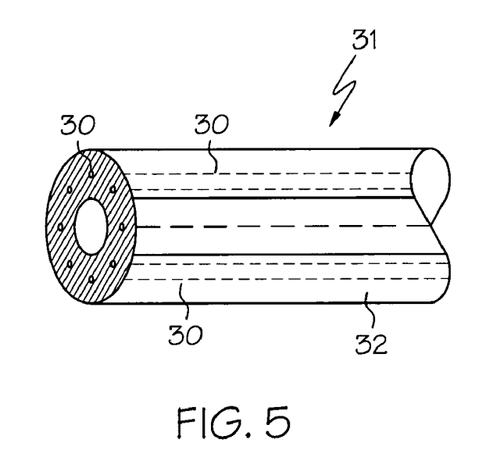
FIG. 5 is a perspective view of the embodiment shown in FIG. 4.

This embodiment is depicted by the tubular parisons in FIGS. 4 and 5. As shown, cores 30 are suspended through out the parison 31 in a matrix 32 which may be composed of any material suitable for constructing a semi-compliant balloon as have been described above. The cores 30 are composed of a material which has a more limited ability to stretch than the matrix material, and when the cores are collectively oriented in the same direction, the structures exhibit an increased longitudinal stability when inflated beyond initial or nominal diameter.

In selecting appropriate materials for the fibrils of cores 30 and matrix 32 it is important to select materials which provide adequate adhesion to one another. If adhesion is insufficient between the cores 30 and the surrounding matrix 32 longitudinal growth of the balloon produced from parison 31 will not be restricted as the more expansive matrix material may slip past the individual cores. A further important attribute of the cores 30 is the bulk elongation of the material. The bulk elongation of the cores 30 is typically less than that of the matrix 32. In preferred embodiments the bulk elongation of the cores 30 may be 200% or less and in some embodiments may be 150% or less. In order to avoid core breakage prior to balloon bursting, it is desirable that if the material from which the cores are constructed exhibit a higher tensile strength than the material of which the matrix is constructed.

Figure 6:
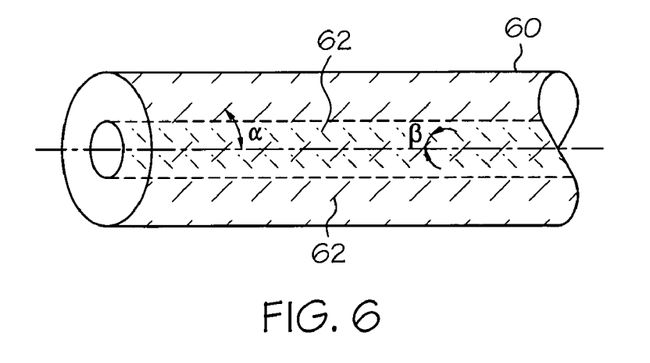
FIG. 6 is perspective view of a dilatation balloon preform in a tubular parison form constructed from micro-composite material wherein the inner and outer fibril components have been oriented diagonally to the longitudinal axis of the tubular preform and in crossing relationship relative to each other by use of a counter-rotating extrusion die.
Figure 7:
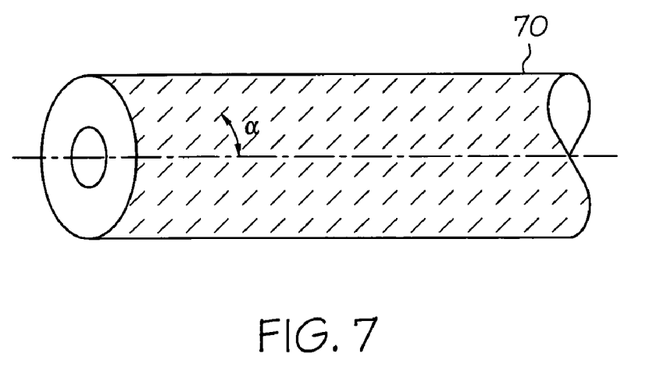
FIG. 7 is another perspective view of only the outer surface of a dilatation balloon preform constructed from micro-composite material wherein the fibril component is oriented diagonally to the longitudinal axis of the tubular preform by use of a rotating die.
Figure 8:
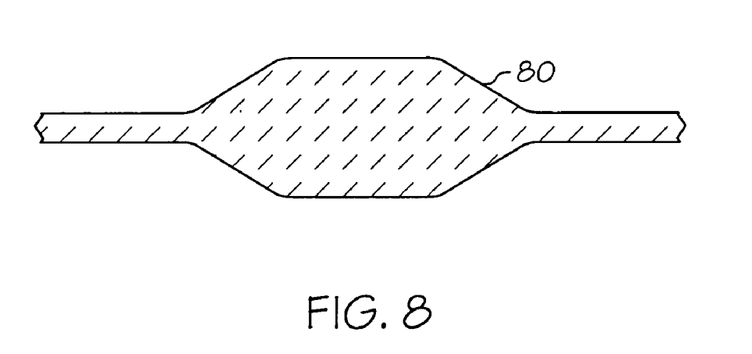
FIG. 8 is a schematic side-view of a blow molded dilatation balloon constructed from micro-composite material depicting the fibril component oriented diagonally to the longitudinal axis of the balloon.

FIG. 6–8 pertain to alternative embodiments in which the fibers of the balloon are orientated diagonally relative to the longitudinal axis of the balloon. In FIG. 6 there is depicted a parison 60 for a balloon in which, in addition to using a high puller speed during extrusion, a counter rotating die was used. The counter rotating die has a mandrel which rotates in one direction and a concentric outer die which rotates in the opposite direction, the parison is extruded through the space between the two. The resulting parison has fibers 62 orientated diagonally to the parison axis 64 in one direction at the outside surface (angle a) and changing gradually as one passes through the material in a direction transverse to the axis 64 to a second direction (angle β) at the inside surface, the angles determined by outer die/mandrel rotation speeds and puller speed. The angles α and β may be about 0 degrees to about 90 degrees, in some embodiment the angles α and β may be about 15 degrees to about 75 degrees, and in some embodiments the angles α and β may be about 30 to about 60 degrees. If one or the other of the outer die or the mandrel are held stationary while the other is rotated, angle α or angle β may be parallel to the axis 64.

In FIG. 7 there is depicted a parison 70, having diagonally oriented fibers formed by relative rotation of the die and puller. For instance only the outer die or mandrel may be rotated so that the fibers become orientated at angle a throughout the entire thickness of the parison.

FIG. 8 depicts the outer surface orientation of a balloon 80 made from a parison of either FIG. 6 or FIG. 7. In the balloon body the fibers retain an angular orientation relative to the balloon axis and provide resistance to both longitudinal and radial expansion beyond the nominal or molded dimensions.

Figure 9:
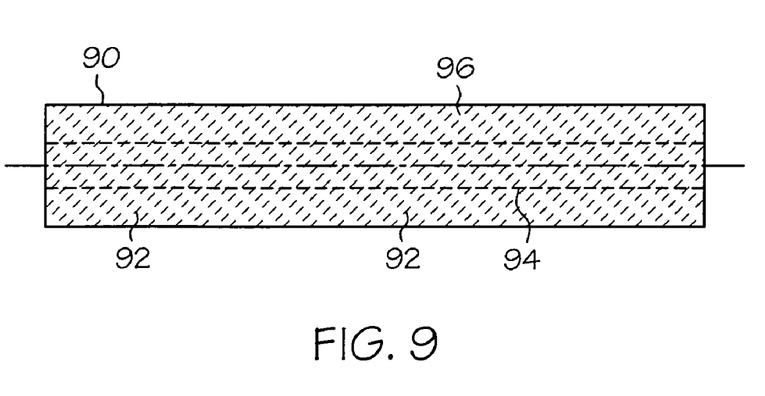
FIG. 9 is a side view of a parison for producing a balloon of an alternative balloon of the invention.

Angular or helical orientation can also be provided in a modification of the extruded fiber core reinforced balloons of FIGS. 4 and 5. Instead of orientating the cores 30 parallel to the axis of the parison, as shown in FIG. 5, the cores may be extruded as helical coils embedded in the matrix polymer material. FIG. 9 depicts such a parison 90 in which the spiraling core fibers are depicted by phantom lines 92. The parison of FIG. 9 has a cross-section as in FIG. 4. Parison 90 may be produced rotating by the die which produces the core fibers 92. Another way to achieve the spiral structure is to rotate the tubing after it exits the die. For instance, a center mandrel which produces the lumen 94 may be rotated to twist the extrusion as it exits the die orifices. As with previous embodiments the core fibers 92 may have a higher tensile strength and lower bulk elongation than the surrounding matrix material 96.

Figure 10:
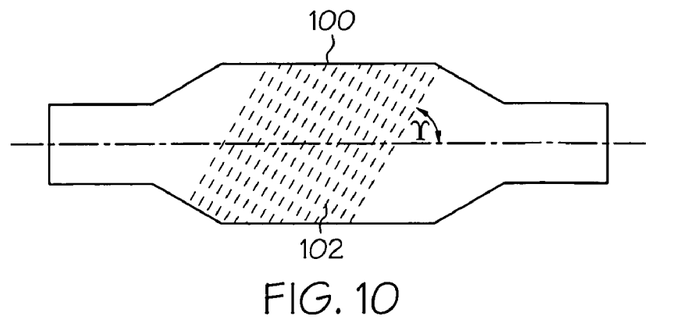
FIG. 10 is a side view of a balloon produced from a parison as in FIG. 9, shown at nominally inflated diameter.
Figure 11:
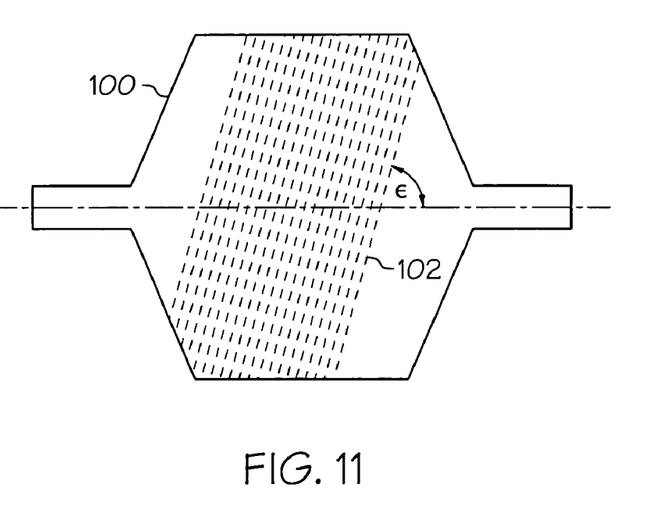
FIG. 11 is a view as in FIG. 9, shown at a diameter expanded beyond nominal diameter.

Helical fiber orientations, i.e. fibers which extend longitudinally, but from side view are diagonally disposed to the tube axis, produce balloons which can achieve hinged balloon distention curves. Angular orientation of the fibers in the parison produces a balloon 100 with angular orientation in the balloon body as shown by FIG. 10 where some of the fibers 102 are shown by the phantom lines. At a first inflated diameter, for instance the nominal diameter depicted in FIG. 10, the fibers form an angle γ relative to the longitudinal axis. As the balloon is further expanded, the fiber orientation angle increases to a greater angle ∈, shown in FIG. 11. The closer the fiber angle comes to a perpendicular orientation the greater the resistance they provide to further diameter growth and radial expansion. The balloon of FIG. 8 behaves in a similar manner.

Advantages for balloons employed in angioplasty, stent placement and other medical applications of "hinged" growth profiles, in which the balloon initially grows at a relatively rapid rate but at higher pressures grows more slowly, have been recognized previously in angioplasty and stent delivery applications. A relatively high growth rate at lower pressures allows the balloon to be used at a larger range of diameters, while the slow rate of growth at high pressure reduces risk of dissection when a high pressure is required to accomplish a lesion dilatation or a firm stent placement. The present invention provides a method for producing a controlled growth profile as desired simply by controlling an extrusion extraction rate and/or rotation factor.

Figure 12:
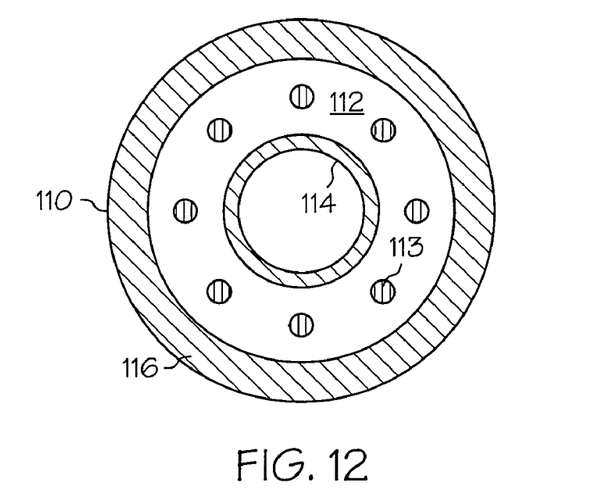
FIG. 12 is a cross-sectional view of a further alternate embodiment of the invention.

In a still further embodiment of the invention the fibers, whether parallel or helically oriented relative to the parison axis, may be incorporated into one or more layers of a multilayer parison. FIG. 12 depicts a cross-section of a three layer parison 110 produced by co-extrusion which has an intermediate layer 112 with embedded reinforcing core fibers 113, and respective inner and outer layers 114, 116 which are free of fiber reinforcement. The fibers 113 may be longitudinally or helically disposed around the longitudinal axis of the parison. Alternative embodiments of such structures include two-layer structures with the fibers on the inner or the outer layer, or both layers but at different orientations; three layer or more layer structures with two or more fiber-containing layers, and embodiments in which, in some or all of the fiber-containing layers, the fibers are oriented microfibers such as LCP fibers oriented in the manner of any of FIG. 1, 6 or 7.

In preferred embodiments of a multi-layer balloon there can be from 7 to about 50, preferably from about 9 to about 15, total polymer layers alternating between (A) fiber-free compliant or semi-compliant polymer, for instance a block copolymer comprising polyamide blocks and polyether blocks such as PEBAX® 7033 or 7233, or a polyamide such as nylon 12, or nylon 6, and (B) blends of the same polymer with about 5–50% by weight, more preferably approximately 10–20% by weight, of an LCP polymer, such as VECTRA® LKX 1111. The ratio A/B of the total thickness of the two types of layers, respectively, being from about 5 to about 15, more preferably about 8–10. A=50–95%; preferred at 90%; B=5–50%, preferred at 10%.

Based on the above description it should be understood that several different polymers with a wide range of characteristics may be used to form a longitudinal or longitudinal and radial stabilized balloon of the present invention. The invention is further illustrated by the following non-limiting examples.

EXAMPLE 1

A matrix component of PEBAX® 7033 was mixed with a fibril component of LCP VECTRA LKX 1107 at the ratio of 95% to 5% respectively by weight. The mixture was extruded at a rate of 110 feet/minute line speed into tubing of 0.039 (outer diameter)×0.027 (inner diameter) inch. A 3.5 mm balloon was formed from the resulting tubing by radial expansion at 110 degrees Celsius with blowing pressure of 350 psi. The balloon with double wall thickness of 0.0014 inch was inflated from 4 atm to 13 atm at 1 atm increment and no measurable balloon length change was observed.

EXAMPLE 2

Coextruded 13 layer parisons 0.019×0.034 inches were prepared with alternating A & B layers, the A-layers being PEBAX® 7233, the B-layers being PEBAX® 7233 blended with 15% by weight VECTRA® LKX 1111. The parisons were extruded 30 at 221° C. Balloons of 3.0 mm diameter, 0.00155 inches double wall thickness, were blown. The ETO sterilized balloons had the following characteristics:
Hinged compliance:
    ave. growth rate, 3–9 atm—0.045 mm/atm
    ave. growth rate, 12–18 atm—0.020 mm/atm
Diameter change at nominal pressure after balloon inflated to 18 atm—5.3%
Burst pressure—26–27 atm
Burst Strength—23201 psi
Longitudinal growth 12 atm to 18 atm—5.9%

EXAMPLE 3

Two extruders are utilized to extrude a plurality of stripes 113 over a metal core. The parison 110 is rotated in one direction with the core at 2000 rpm to produce the helically oriented tubing, such as may be seen in FIGS. 9–12. The core fibers 113 may be MXD6 aromatic nylon from Mitsubishi Gas Chemical. The tubing material, such as layers 112, 114 and 116 may be one or more base polymer materials such as PEBAX® 7233. The stripes 113 are evenly distributed along the circumference of the tubing and located at the middle of the tubing wall.

In the present example, a 3.0 mm balloon was formed from a tube having an internal diameter of 0.021 inches and an outer diameter of 0.037 inches at 95° C. and at 400 psi pressure. The balloon burst at 311 psi with double wall thickness of 0.00145 inch. The balloon length change was 2.3 percent from 6 atm to 12 atm, and 3.2 percent from 12 to 18 atm.

For comparison purposes in regard to Example 3, tubing of 100 percent PEBAX® 7233, with dimensions of 0.0348 (outer diameter)×0.0200 (inner diameter), is used to form a 3.0 mm balloon at 95° C. at 400 psi blowing pressure. The formed balloon with double wall thickness of 0.00140 inches burst at 353 psi. The balloon length change was 3.5 percent from 6 atm to 12 atm, and 5.5 percent from 12 to 18 atm.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each single dependent claim format which creates a dependency from a prior antecedent-possessing claim other than the specific claim listed in such dependent claim below it.

What is claimed is:

1. A medical balloon which has a determined preinflation diameter and length, a longitudinal axis, and restricted longitudinal and radial characteristics, comprising: a polymer matrix material; and a plurality of fibers distributed in the polymer matrix material to provide reinforcement thereof; the fibers are distributed in a selected direction relative to the longitudinal axis of the balloon and composed of polymeric material which has a greater tensile strength than the polymer matrix material, the fiber polymeric material selected from the group consisting of polyetheretherketone, polyphenylene sulfide, aromatic nylon, rigid polyurethane, polyester, copolyester, polyester blends, polyester/polyurethane blends and fluoropolymer, which is stronger than the polymer matrix material, and has a bulk elongation of 200% or less, which is less than the bulk elongation of the polymer matrix material, wherein the cores of the fibers are formed by phase separation from the melt upon extrusion of a melt blend of the fiber polymeric material and the polymer matrix material, and the fibers operatively adhere to the polymer matrix material.

2. A medical balloon as in claim 1, the medical balloon has a wall composed of a plurality of laminate layers, at least one layer of which comprises said polymer matrix material and said fibers.

3. A medical balloon as in claim 2 wherein said laminate layers comprise an alternating series of fiber-containing and fiber-free layers.

4. A medical balloon as in claim 3 with at least 7 of said layers.

5. A medical balloon as in claim 1, wherein the fibers are distributed in the matrix material helically relative to the longitudinal axis of the balloon.

6. A medical balloon as in claim 2 wherein the fibers are distributed in the matrix material helically relative to the longitudinal axis of the balloon.

7. A medical balloon as in claim 6 wherein said fibers have a diameter of from 0.01 to about 10 microns.

8. A medical balloon as in claim 2 with a body portion wherein the fibers are oriented substantially parallel to the longitudinal axis of the balloon.

9. A medical balloon as in claim 8 wherein said fibers have a diameter of from 0.01 to about 10 microns.

10. A medical balloon which has a determined preinflation diameter and length, a longitudinal axis, and restricted longitudinal and radial characteristics, comprising from 7 to 50 total polymer layers, which alternate between layers (A) and (B); layer (A) is composed of a polymer material and layer (B) is composed of a polymer matrix material and a plurality of fibers distributed in the polymer matrix material to provide reinforcement thereof; the fibers are distributed in a selected direction relative to the longitudinal axis of the balloon, and composed of polymeric material which has a greater tensile strength than the polymer matrix material, the fiber polymeric material selected from the group consisting of polyetheretherketone, polyphenylene sulfide, aromatic nylon, rigid polyurethane, polyester, copolyester, polyester blends, polyester/polyurethane blends and fluoropolymer, which is stronger than the polymer matrix material, and has a bulk elongation of 200% or less, which is less than the bulk elongation of the polymer matrix material, wherein the cores of the fibers are formed by phase separation from the melt upon extrusion of a melt blend of the fiber polymeric material with the polymer matrix material, and the fibers operatively adhere to the polymer matrix material.

11. A medical balloon as in claim 10 wherein the ratio A/B of the total thickness of the two types of layers, (A) and (B) respectively, is from about 5 to about 15.

12. A medical balloon as in claim 11 wherein said ratio is from 8 to 10.

13. A medical balloon as in claim 10 wherein the polymer material of layer (A) and the polymer matrix material of layer (B) are the same.

14. A medical balloon as in claim 10 where in the layers (B) the polymer matrix material comprises an LCP polymer present in an amount of from about 5 to about 25% by weight.

15. A medical balloon as in claim 10, wherein at least some of said layers are formed from an extruded melt blend of a polymer matrix material and an LCP polymer material which formed fibers by phase separation from the melt blend, and the LCP polymer fibers are oriented substantially in a longitudinal or helical direction relative to the longitudinal axis of the balloon.

16. A medical balloon as in claim 10 wherein said polymer material of layer (A) is compliant or semi-compliant and said polymer matrix material of layer (B) is compliant or semi-compliant.

17. A medical balloon as in claim 10 wherein said polymer material of layer (A) and said polymer matrix material of layer (B) are individually selected from the group consisting of block copolymers comprising polyamide blocks and polyether blocks, block copolymers comprising polyester blocks and polyether blocks, and mixtures thereof.

* * * * *

UNITED STATES PATENT AND TRADEMARK OFFICE
CERTIFICATE OF CORRECTION

| | |
|---|---|
| PATENT NO. | : 6,977,103 B2 |
| APPLICATION NO. | : 09/885568 |
| DATED | : December 20, 2005 |
| INVENTOR(S) | : John Jianhua Chen et al. |

It is certified that error appears in the above-identified patent and that said Letters Patent is hereby corrected as shown below:

On Title Page, Column 2, Line 29, (74) *Attorney, Agent, or Firm,* delete "Vibas" and insert --Vidas--;

Signed and Sealed this

Twenty-first Day of November, 2006

JON W. DUDAS
*Director of the United States Patent and Trademark Office*